(12) United States Patent
Burckhardt

(10) Patent No.: US 10,499,962 B2
(45) Date of Patent: Dec. 10, 2019

(54) BONE PLATE TEMPLATE SYSTEMS HAVING ONE OR MORE REMOVABLE SEGMENTS AND METHODS FOR USING THE SAME

(71) Applicant: Flower Orthopedics Corporation, Horsham, PA (US)

(72) Inventor: Oliver Burckhardt, Philadelphia, PA (US)

(73) Assignee: FLOWER ORTHOPEDICS CORPORATION, Philadelphia, PA (US)

( * ) Notice: Subject to any disclaimer, the term of this patent is extended or adjusted under 35 U.S.C. 154(b) by 867 days.

(21) Appl. No.: 14/649,746

(22) PCT Filed: Dec. 5, 2013

(86) PCT No.: PCT/US2013/073292
§ 371 (c)(1),
(2) Date: Jun. 4, 2015

(87) PCT Pub. No.: WO2014/089285
PCT Pub. Date: Jun. 12, 2014

(65) Prior Publication Data
US 2015/0313652 A1    Nov. 5, 2015

Related U.S. Application Data

(60) Provisional application No. 61/734,003, filed on Dec. 6, 2012.

(51) Int. Cl.
*A61B 17/80* (2006.01)

(52) U.S. Cl.
CPC .................................. *A61B 17/80* (2013.01)

(58) Field of Classification Search
CPC ............................ A61B 17/80; A61B 17/8085
See application file for complete search history.

(56) References Cited

U.S. PATENT DOCUMENTS 4,966,599 A * 10/1990 Pollock .............. A61B 17/1735
206/457
5,647,872 A * 7/1997 Gilbert ............... A61B 17/7059
606/280

(Continued)

*Primary Examiner* — Nicholas W Woodall
(74) *Attorney, Agent, or Firm* — Riverside Law LLP

(57) ABSTRACT

Bone plate template systems and methods determine a suitable bone plate implant from a plurality of bone plate implants. The systems and methods have a first bone plate implant having a first length, and a second bone plate implant having a second length that is less than the first length of the first bone plate implant. The systems and methods have a bone plate template having a shape and a length defined between a first end and a second end located opposite to the first end, wherein at least a portion of the shape of the bone plate template corresponds to at least portions of a shape of at least one of the first and second bone plate implants. The bone plate template has at least one removable segment located adjacent to the second end of the bone plate template, wherein a connecting section of the bone plate template has a width and connects the at least one removable segment to the first end of the bone plate template. The bone plate template displays first indicia indicative of the first bone plate and the at least one removable segment displays second indicia indicative of the second bone plate.

16 Claims, 5 Drawing Sheets

(56) References Cited

U.S. PATENT DOCUMENTS

| | | | |
|---|---|---|---|
| 5,690,631 A * | 11/1997 | Duncan | A61B 17/8085 606/281 |
| 5,718,705 A * | 2/1998 | Sammarco | A61B 17/8085 606/260 |
| 5,746,742 A | 5/1998 | Runciman et al. | |
| 7,717,946 B2 * | 5/2010 | von Oepen | A61B 17/8085 264/323 |
| 2007/0083204 A1 | 4/2007 | Sidebotham | |
| 2009/0171398 A1 | 7/2009 | Phillips et al. | |
| 2010/0292697 A1 * | 11/2010 | von Oepen | A61B 17/8085 606/70 |

* cited by examiner

BONE PLATE TEMPLATE SYSTEMS HAVING ONE OR MORE REMOVABLE SEGMENTS AND METHODS FOR USING THE SAME

This application is the U.S. national phase application filed under 35 U.S.C. § 371 claiming benefit to International Patent Application No. PCT/US2013/073292, filed Dec. 5, 2013, which is entitled to priority under 35 U.S.C § 119(e) to U.S. Provisional Patent Application No. 61/734,003, filed Dec. 6, 2012, each of which applications are incorporated by reference herein in their entireties.

FIELD OF THE DISCLOSURE

The present disclosure relates to one or more bone plate template systems having one or more removable bone plate templates, one or more removable segments and one or more methods for using the bone plate template systems. The present bone plate template systems and methods may be used to identify one or more bone plates having a correct, suitable or appropriate sizes, shapes and/or lengths to be utilized in a bone plate fixation or implant procedure. The bone plate template systems may have one or more removable bone plate templates and/or one or more removable segments that may be removed or separated from the bone plate template systems to determine, indicate and/or identify a correct, suitable or appropriate size, shape and/or length for a bone plate to be affixed to a damaged bone of a patient or implanted into the patient during a bone fixation or implant procedure. One of the sides of the bone plate template systems, the removable bone plate templates and/or the removable segments may have or display indicia which may be used to determine or identify the correct, suitable and/or appropriate bone plate to be utilized during the bone plate fixation or implant procedure. Each bone plate template system and corresponding bone plate implants may be individually sterilized and individually packaged such that each bone plate template system and bone plate implants are immediately ready for use in the procedure after unpackaging from their individual sterile-packaging.

Bone plates are traditionally delivered to the operating room in various shapes and sizes so that the surgeon can choose the suitable or appropriate bone plate to be used to complete the surgical procedure. The surgeon is traditionally required to hold many different bone plates, having different sizes, shapes and/or lengths, near an operating sight of the patient to determine or identify which one of the many different bone plates is correctly shaped and/or sized for repairing the damaged bone of the patient based on the one or more dimensions of the operating sight and/or the damaged bone of the patient. As a result, the many different bone plates that were handled by the surgeon, but not used by the surgeon during the procedure, need to be, and are required to be, subsequently sterilized for future use or discarded all together. Either subsequently sterilizing the unused, but handled, different bone plates or discarding the unused, but handled, different bone plates is costly, time consuming and/or labour intensive, and may even result in subsequent damage to the unused, but handled, bone plates or insufficient sterilization of the unused, but handled, bone plates.

The present bone plate template systems and methods provide one or more removable bone plate templates connected to a main body which may be easily removed, without the use of a tool, in the operating room or may be removed or separated, by hand, during the procedure. In embodiments, one or more of the removable bone plate templates may have one or more removable segments which may be easily removed, without the use of a tool, in the operating room or may be removed, by hand, during the procedure. Each bone plate template system is delivered to the operating room in individual sterile-packaging within a kit container which may have one or more individually sterile-packaged sterile containers. The one or more individually sterile-packaged containers may each contain a sterile bone plate and/or a set of sterile screws sized for use with the bone plate.

Some of the individually packaged sterile containers may contain other components necessary for completing the bone plate fixation or implant procedure. In an embodiment, one of the bone plate template systems and/or removable bone plate templates may have a size, shape and/or length that corresponds to a size, shape and/or length of a largest and/or longest bone plate that is included in the kit container. During the procedure, a surgeon may hold one or more bone plate template systems and/or removable bone plate template up to, near or adjacent to the operating site on the patient to determine or identify the correct, suitable or appropriate size, shape and/or length of the bone plate that is needed to complete the procedure. Then, unless the largest bone plate in the kit container is the correct size, shape and/or length necessary for completing the procedure based on the operating site, the surgeon may tear off or physically remove or separate one or more of the removable segments from the bone plate template system and/or removable bone plate template in order to determine and/or identify the suitable bone plate implant having the suitable size, shape and/or length to be utilized during the procedure based on the one or more dimensions of the operating site and/or damaged bone of the patient.

The removable segments, including the removable segments separated from the bone plate template system, may be stamped or marked with and/or display indicia, such as, for example, letters, numbers, symbols, designs, graphics and/or combinations thereof. As a result, the indicia on the removable segments separated from the bone plate template system may be used, inspected or observed to determine and/or identify the suitable bone plate, having the suitable size, shape and/or length, for completing the procedure. Subsequently, the suitable bone plate, identified or determined by the indicia of the removable segments separated and/or removed from the bone plate template system, may then be selected from the kit container, unpackaged from its individual sterile-packaging, and used to complete the bone plate fixation and/or implant procedure. As a result, only the suitable bone plate, that is needed to complete the procedure, is unpackaged and/or handled in the operating room prior to affixation to the bone of the patient or implantation into the patient. Other differently shaped and/or sized bone plates, included in the kit container, that are not suitable for completing the procedure remain sterile in their individual sterile-packaging within the kit container for subsequent use in a different subsequent procedure.

SUMMARY OF THE DISCLOSURE

In embodiments, a bone plate template may identify a suitable bone plate implant. The bone plate template may have a length defined between a first end of the bone plate template and a second end of the bone plate template located opposite to the first end of the bone plate template, wherein at least a portion of the length of the bone plate template has a shape that corresponds to at least a portion of a shape of the suitable bone plate implant. Further, the bone plate template may have a first portion of the bone plate template having a first width and located adjacent to the first end of the bone plate template and at least one first removable segment of the bone plate template having a second width and located adjacent to the second end of the bone plate template. Moreover, the bone plate template may have at least one connecting section of the bone plate template connecting the first portion to the at least one first removable segment, wherein the at least one connecting section has a third width that is less than the first width of the first portion and the second width of the at least one removable segment.

In an embodiment, the bone plate template may have first indicia displayed on the at least one first removable segment, wherein the first indicia is indicative of a first bone plate implant having a first length.

In an embodiment, the bone plate template may have at least one second removable segment located between and connected to the first portion and the at least one first removable segment.

In an embodiment, the bone plate template may have second indicia displayed on the at least one second removable segment, wherein the second indicia is indicative of a second bone plate implant having a second length that is less than the first length of the first bone plate implant.

In an embodiment, third indicia ma be displayed on the bone plate template that is indicative of a third bone plate implant having third length that is less than the first length of the first bone plate implant and the second length of the second bone plate implant.

In an embodiment, the bone plate template may be stored within individual sterile-packaging.

In an embodiment, the bone plate template may have a thickness and may be made of a frangible material.

In an embodiment, the thickness of the bone plate template, the frangible material of the bone plate template or the third thickness of the at least one connecting section may be configured such that the bone plate template is breakable at the at least one connecting section without use of a tool.

In embodiments, a method may determine a suitable bone plate implant from a plurality of bone plate implants, wherein each bone plate implant of the plurality of bone plate implants has a different length. The method may position a bone plate template adjacent to an operating site of a patient, wherein the bone plate template, has a shape and an original length defined between a first end and a second end located opposite to the first end, and comprises at least one removable segment located along the length of the bone plate template, wherein at least a portion of the shape of the bone plate template corresponds to at least a portion of at least one bone plate implant of the plurality of bone plate implants. Further, the method may separate the at least one removable segment from the bone plate template so that the bone plate template has a remaining length that is less than the original length of the bone plate template, wherein the remaining length of the bone plate template is similar to a length associated with the operating site of the patient. Moreover, the method may identify the suitable bone plate implant from the plurality of bone plate implants based on the remaining length of the bone plate template or the at least one removable segment separated from the bone plate template, wherein the suitable bone plate implant has a suitable length that is similar to the length associated with the operating site of the patient.

In an embodiment, prior to positioning the bone plate template adjacent to the operating site of the patient, the bone plate template may be stored in individual sterile-packaging, and further wherein each bone plate implant of the plurality of bone plate implants is stored in an individual sterile-package.

In an embodiment, the individual sterile-packaging storing the bone plate template and each of the bone plate implants may be provided in a kit container.

In an embodiment, a separated removable segment may be located opposite to the second end of the bone plate template displays indicia indicative of the suitable bone plate implant having the suitable length.

In an embodiment, the method may select the suitable bone plate implant from the plurality of bone plate implants based on the indicia displayed on the separated removable segment that is located opposite to the second end of the bone plate template.

In an embodiment, the method may select the suitable bone plate implant from the plurality of bone plate implants by matching indicia associated with the suitable bone plate to the indicia displayed on the separated removable segment located opposite to the second end of the bone plate template.

In an embodiment, the bone plate template may be made of frangible material such that the at least one removable segment separates from the bone plate template without use of a tool.

In embodiments, a bone plate template system may determine a suitable bone plate implant from a plurality of bone plate implants. The system may have a first bone plate implant having a first length and a second bone plate implant having a second length that is less than the first length of the first bone plate implant. Further, the system may have a bone plate template having a shape and a length defined between a first end and a second end located opposite to the first end, wherein at least a portion of the shape of the bone plate template corresponds to at least portions of a shape of at least one of the first and second bone plate implants, wherein the bone plate template comprises at least one removable segment located adjacent to the second end of the bone plate template, wherein a connecting section of the bone plate template has a width and connects the at least one removable segment to the first end of the bone plate template, wherein the bone plate template displays first indicia indicative of the first bone plate and the at least one removable segment displays second indicia indicative of the second bone plate.

In an embodiment, the width of the connecting section may be less than other widths of the bone plate template located between first and second ends of the bone plate template.

In an embodiment, the bone plate template may be made of a frangible material such that the at least one removable segment is separable from the bone plate template without use of a tool.

In an embodiment, the first length of the first bone plate implant may be less than the second length of the second bone plate implant.

In an embodiment, each of the first bone plate implant, the second bone plate implant and the bone plate template may be individually packaged in sterile-packaging.

In an embodiment, a bone plate template system may determine a suitable bone plate implant from a plurality of bone plate implants. The system may have a first removable bone plate template, wherein at least a portion of a shape of the first removable bone plate template corresponds to at least a portion of a shape of a first bone plate implant. Further, the system may have a second removable bone plate template removably connected to the first removable bone plate template, wherein at least a portion of a shape of the second removable bone plate template corresponds to at least a portion of the a shape of a second bone plate implant, wherein the shape of the first removable bone plate template is different than the shape of the second removable bone plate template.

In an embodiment, the first removable bone plate template or the second removable bone plate template may have one or more removable segments.

In an embodiment, the system may have a main body removably connecting the first and second removable bone plate templates.

In an embodiment, the main body may have connecting points removably connecting the first and second removable bone plate templates to the main body.

In an embodiment, the system may have at least one removable segment removably connecting the first and second removable bone plate templates.

In an embodiment, the system may have first indicia, displayed on the first removable bone plate template, indicative of the first bone plate implant, and second indicia, displayed on the second removable bone plate template, indicative of the second bone plate implant.

BRIEF DESCRIPTION OF THE DRAWINGS

So that the features and advantages of the present disclosure can be understood in detail, a more particular description of the systems and methods may be had by reference to the embodiments thereof that are illustrated in the appended drawings. It is to be noted, however, that the appended drawings illustrate only some typical embodiments of the present systems and methods and are therefore not to be considered limiting of its scope, for the systems and methods may admit to other equally effective embodiments.

DETAILED DESCRIPTION OF THE DISCLOSURE

The present bone plate template systems and methods may have one or more removable bone plate templates and/or removable segments which may easily be removed, without the use of a tool, to determine, identify and/or select a correct, suitable and/or appropriate bone plate (hereinafter "suitable bone plate") from a plurality of differently sized and/or shaped bone plates (hereinafter "plurality of bone plates") for completing a surgical procedure, a bone plate fixation, bone plating or implantation procedure (hereinafter "the procedure"). After being separated from the bone plate template system, the separated bone plate templates and/or separated segments themselves, or indicia displayed thereon, may be utilized, inspected or observed to determine, identify and/or select the suitable bone plate from the plurality of bone plates. The suitable bone plate may be subsequently used for fixation to or implantation into a patient during the procedure. Alternatively, the bone plate template, whereby the separated segments may have been removed therefrom, may be utilized, inspected or observed to determine, identify and/or select the suitable bone plate from the plurality of bone plates.

In embodiments, the bone plate template system, the removable bone plate templates and/or each bone plate of the plurality of bone plates are individually sterilized and individually packaged such that, during the surgical procedure, only the bone plate template system, the removable bone plate templates and/or the suitable bone plate are opened or unpackaged and the remaining unused components and/or the unused bone plates of the plurality of bone plates remain in their individual sterile-packaging for use during subsequent procedures. The bone plate template systems and/or the removable bone plate templates are single-use disposable medical components, such that, after completion of the procedure, the bone plate template systems and/or the removable bone plate templates along with any separated removable segments may be disposed without requiring any further attention from the surgical staff and/or medical providers.

Figure 1:
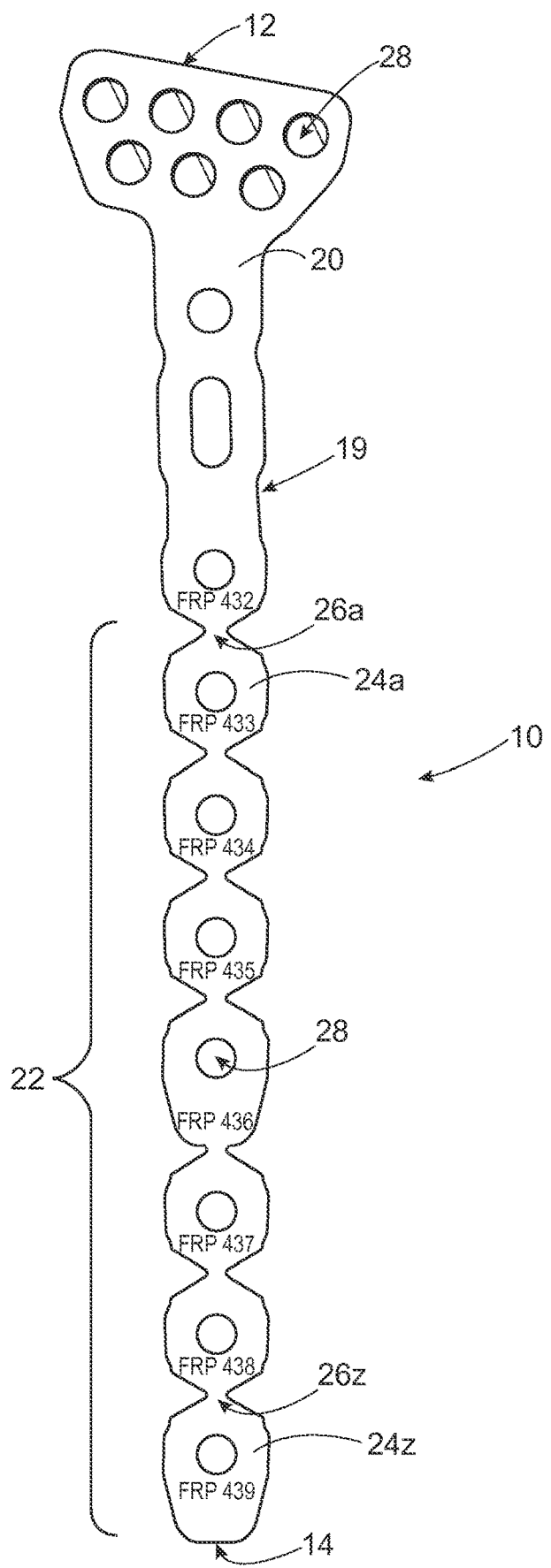
FIG. 1 illustrates a top plan view of a bone plate template system in an embodiment.
Figure 2:
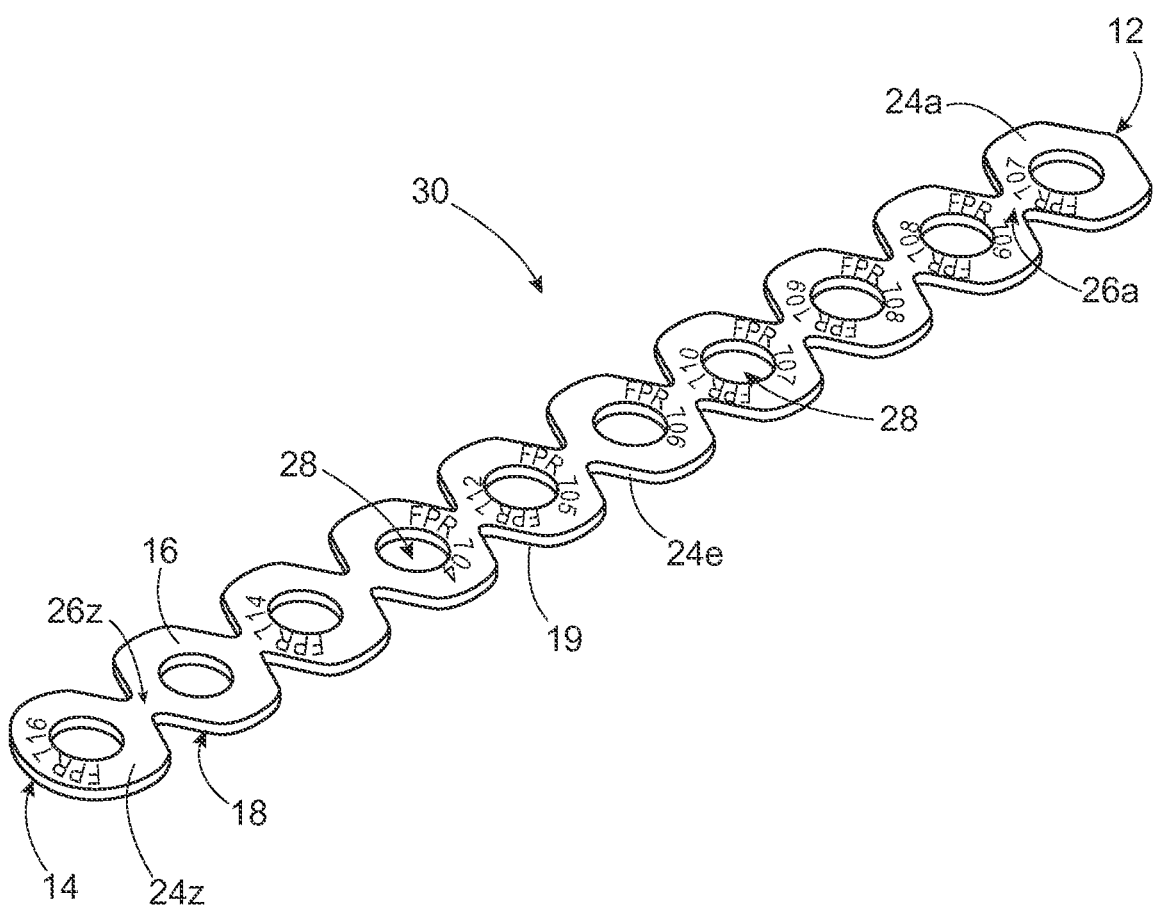
FIG. 2 illustrates a perspective view of a bone plate template system in an embodiment.
Figure 4:
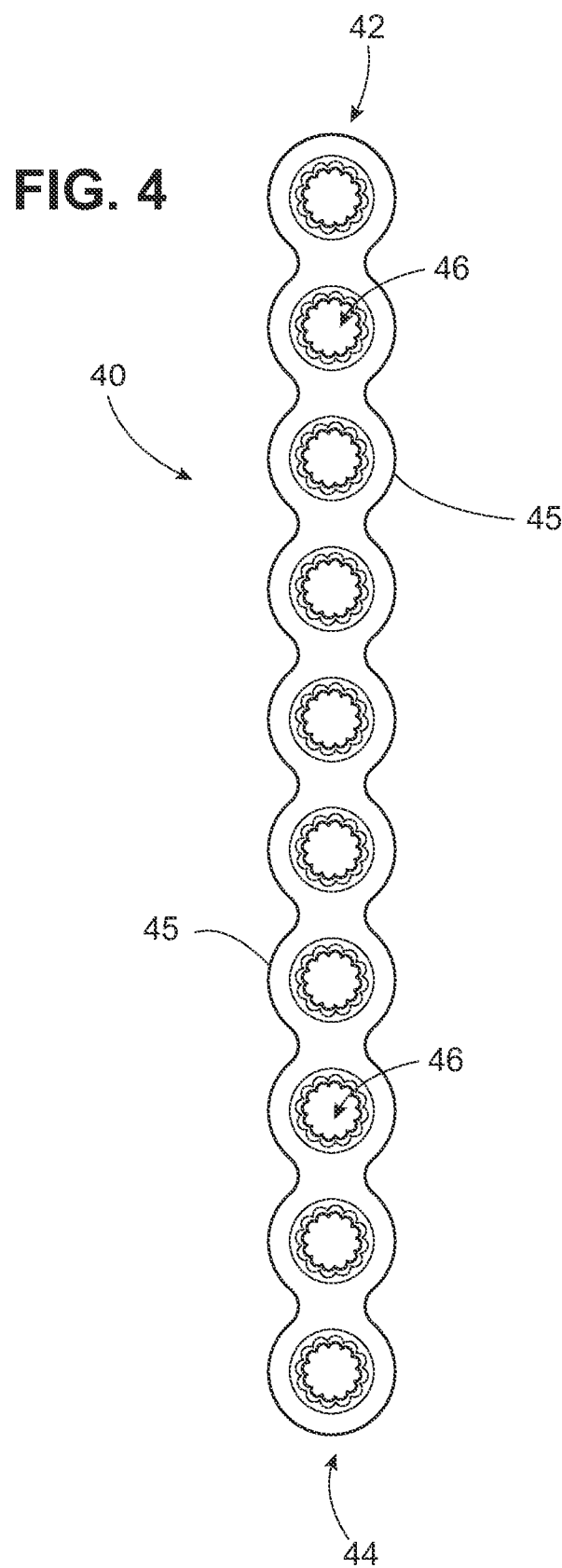
FIG. 4 illustrates a top plan view of at least one bone plate implant that may be provided in a kit container along with the bone plate template system shown in FIG. 2 in an embodiment.
Figure 5:
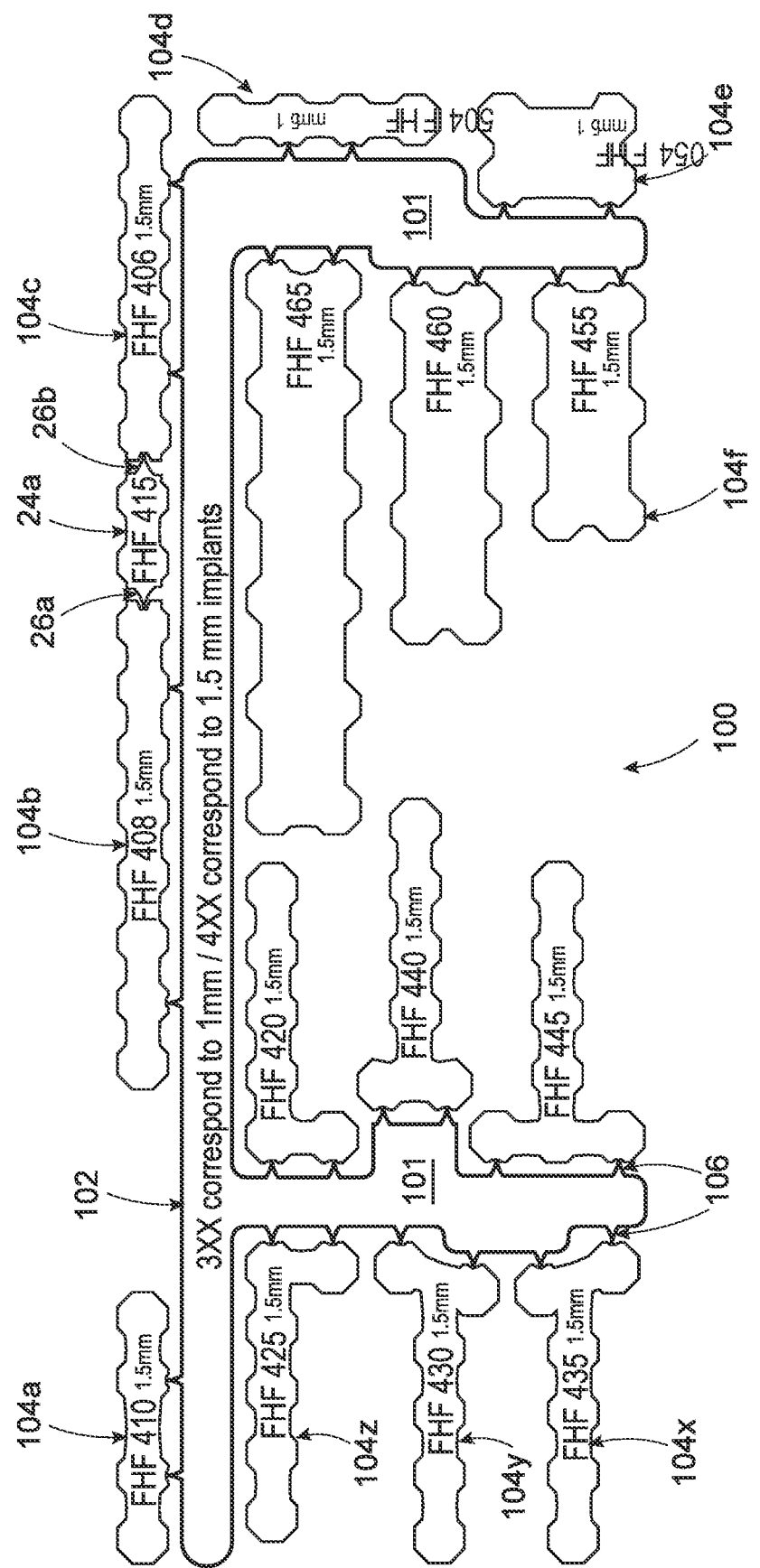
FIG. 5 illustrates a top plan view of bone plate template system having a plurality of bone plate templates connected to a main body of the bone plate template system in an embodiment.

Referring now to the drawings wherein like numerals refer to like parts, a first bone plate template 10 (hereinafter "template 10"), and a second bone plate template 30 (hereinafter "template 30") are shown in FIGS. 1 and 2, respectively. A bone plate template system 100 (hereinafter "system 100") having a plurality of removable bone plate templates 104a-104z (hereinafter "templates 104a-104z") is shown in FIG. 5. Each of the template 10, the template 30 and/or the templates 104a-104z (collectively known hereinafter as "templates 10, 30, 104a-104z") may have a general shape and/or an outer perimeter that may be the same as, similar to or corresponds to a general shape and/or an outer perimeter of at least one corresponding bone plate implant that is provided in a surgical procedure kit container (not shown in the drawings). Further, each of the templates 10, 30, 104a-104z may have a length that is the same as, similar to or corresponds to a length of at least one corresponding bone plate provided in the kit container. For example, template 30 (as shown in FIG. 2) has a general shape, outer perimeter, width and/or length that is the same as, similar to or corresponds to a general shape, outer perimeter, width and/or length of a corresponding bone plate implant, such as, for example, bone plate implant 40 (hereinafter "plate 40") as shown in FIG. 4. The template 10 may have a general shape, outer perimeter, width and/or length that may be the same as, similar to or corresponding to a general shape, outer perimeter, width and/or length of at least one corresponding bone plate implant (not shown in the drawings). Each of the templates 104a-104z may have a general shape, outer perimeter, width and/or length that may be the same as, similar to or corresponding to a general shape, outer perimeter, width and/or length of at least one corresponding bone plate implant (not shown in the drawings).

In embodiments, only portions of the templates 10, 30, 104a-104z have general shapes, outer perimeters, widths and/or lengths that may be the same as, similar to or corresponding to general shapes, outer perimeters, widths and/or lengths of at least portion of at least one corresponding bone plate implant (not shown in the drawings). In an embodiment, the templates 10, 30, 104a-104z may have a general shape and/or an outer perimeter that corresponds to or substantially corresponds to a general shape and/or an outer perimeter of one or more corresponding bone plate implants (hereinafter "corresponding plates") which may be provided in a kit container along with the templates 10, 30, 104a-104z, respectively.

For example, the kit container, including the template 30, the plate 40 and corresponding plates that have corresponding or similar general shapes or outer perimeters with respect to the system 30 and the plate 40, may be utilized by a surgeon or medical provider to complete at least one procedure. The corresponding plates, included in the kit container, may have corresponding general shapes and/or outer perimeters that are the same as, similar to or correspond to the general shapes and/or outer perimeters of the template 30 and plate 40; however, each of the corresponding plates of the kit container may have different overall lengths which may be less than or shorter than overall lengths of the template 30 and/or the plate 40. In embodiments, each of the corresponding plates of the kit container may have at least one different dimension with respect to each other, the template 30 and/or the plate 40. For example each corresponding plate of the kit container may have different heights, different widths, different thicknesses and/or different lengths when compared to heights, widths, thicknesses and/or lengths of other corresponding plates, the template 30 and/or the plate 40 provided in the kit container.

In embodiments, the kit container comprises the corresponding plates and the plate 40 whereby each corresponding plate has a different length when compared to the each other and a shorter length than the overall length of the plate 40. As a result of these different lengths, the surgeon or medical provider must determine, identify and select a suitable bone plate, from the plate 40 and the corresponding plates of the kit container, having a correct, suitable or appropriate length (hereinafter "suitable length") for affixing to a damaged bone or for implantation into the patient. The suitable length of the suitable bone plate is determined or identified based on a length associated the operating site or the damaged bone of the patient. The suitable length for the suitable bone plate may be determined by visual inspection of the operating site or the damaged bone of the patient or direct comparison of the system 30 and the operating site and/or damaged bone of the patient.

In embodiments, the templates 10, 30, 104a-104z have at least one dimension, such as, for example, a height, a width, a thickness and/or a length that is the same as, similar to, substantially similar to or corresponding to at least one dimension of a largest bone plate implant of the corresponding plates included in the kit container. For example, template 30 may have an overall length that is the same as, similar to or corresponding to an overall length of the longest bone plate implant (hereinafter "longest plate"), such as, for example, plate 40. The other bone plate implants of the corresponding plates provided in the kit container have smaller or shorter overall lengths than the overall lengths of the system 30 and the longest plate (i.e., plate 40).

Based on the shape and/or length associated with the operating site and/or the damaged bone of the patient, the suitable bone plate having the suitable shape and/or length may be the longest bone plate provided in the kit container (i.e., plate 40) or may be one of the corresponding plates having a shorter length than the longest bone plate implant of the kit container. In order to determine the suitable shape and/or length and the suitable bone plate, the surgeon or medical provider may visually inspect the operating site or the damaged bone and utilize one of the templates 10, 30, 104a-104z to determine or identify the shape and/or length associated with the operating site and/or the damaged bone.

After the suitable shape and/or length for the suitable bone plate is determined or identified based on the shape and/or length associated with the operating site and/or the damaged bone, at least a portion of one of the systems 10, 30 may be removed or separated to determine and/or select the suitable bone plate from the plate 40 and the corresponding plates included in the kit container. After the suitable bone plate is determined and/or selected from the kit container, the individually sterile-packaging housing, storing or protecting the suitable bone plate is opened or unpackaged, and the unpackaged suitable bone plate is subsequently affixed to or implanted into the patient during the procedure.

In embodiments, the plate 40 and corresponding plates included in the kit container may be, for example, an anatomic plate, a reconstruction plate or an osteosynthesis plate. In an embodiment, the plate 40 and corresponding plates may be, for example, a veterinary orthopedic implant. Outer surfaces of the plate 40 and corresponding plates may be made of one or more biomedical materials, such as, for example, titanium, silicone, apatite and/or the like. In embodiments, the plate 40 and corresponding plates may be one selected from the group consisting of a hand plate, a foot plate, a reconstruction S-plate, a reconstruction M-plate, a proximal humerus plate, a distal radius plate and an osteosynthesis S-plate. In an embodiment, the hand and/or foot plate may be, for example, a straight plate, a L-plate, an oblique T-plate, a T-plate, a H-plate, a mediocarpal plate, an elongated L-plate, a straight plate with slots, or an angled and/or inclined plate. In an embodiment, the reconstruction S-plate may be, for example, a straight plate or a T-plate. In an embodiment, the distal radius plate may be, for example, volar, narrow L-plate, a volar, narrow R-plate, a volar, wide L-plate, a volar, wide R-plate, a dorsal L-plate, a dorsal R-plate, a volar L-plate or a volar R-plate. The plate 40 and corresponding plates may have a thickness, such as, for example, less than about 4.0 millimetres (hereinafter "mm"), less than about 3.0 mm, less than about 2.0 mm, less than about 1.5 mm or about 1.0 mm. It should be understood that the present disclosure is not limited to a specific embodiment of the plate 40, the one or more biomedical materials on the outer surfaces of the plate 40 and/or the thickness of the plate 40 and/or the corresponding plates. Moreover, the plate 40 may be any bone plate or bone-fixation implant as known to one of ordinary skill in the art.

The system 100, the templates 10, 30, 104a-104z, the plate 40, the corresponding plates and/or the kit container may be used for internal fixation of fractures and/or reconstruction of one or more bones of patients. The one or more bones may include a scapula, olecranon, humerus, radius, ulna, pelvis, distal tibia, fibula, hand bones and/or foot bones of the patients. The internal fixation and/or reconstruction may include compression fractures, intra-articular and/or extraarticular factures, displaced fractures, osteotomies, non-unions and/or mal-unions. Moreover, the system 100, the templates 10, 30, 104a-104z, the plate 40, the corresponding plates and/or the kit container may be used for palmar, ventral, dorsal and/or orthogonal applications. It should be understood that the present disclosure is not limited to a specific embodiment of the one or more bones, the internal fixation, reconstruction and/or application for the system 100, the templates 10, 30, the plate 40, the corresponding plates and/or the kit container.

In embodiments, each of the templates 10, 30, 104a-104z may be one selected from the group consisting of a mediocarpal plate template, a recon plate template, a H & F plate template, a recon T-plate template, a straight osteo plate template, a H-plate template, a dorsal distal radius plate template, volar distal radius plate template, a narrow volar distal radius plate template, a wide volar distal radius plate template, a humerus plate template, a straight osteo plate template, an elongated L-plate template, an angled & inclined plate template, and a straight plate with slots template. The templates 10, 30, 104a-104z may have one or more structural features that correspond to one or more structural features of a bone plate implant, such as, for example, the plate 40. In embodiments, the templates 10, 30, 104a-104z may have outer perimeters, curvatures, indentations, angles, ridges and/or holes which may correspond to outer perimeters, curvatures, indentations, angles, ridges and/or screw holes that may be present in and/or on the plate 40, the corresponding plates and/or other bone plate implants included in the kit container.

In embodiments, the templates 10, 30, 104a-104z may be made of at least one frangible material such that the templates 10, 30, 104a-104z may be broken or separated into pieces or fragments, without the use of a tool, by hands of user, such as, for example, a surgeon, surgical staff member or medical provider. In embodiments, a first portion of the templates 10, 30, 104a-104z may be made of the frangible material and a second portion may be made of a non-frangible material such that the first portion of the templates 10, 30, 104a-104z may be fragmented, broken or separated away from the second portion, without the use of a tool, by hands of the user. The at least one frangible material may include, for example, one or more frangible metal materials, one or more frangible polymer materials, one or more frangible composite materials and/or combinations thereof. In an embodiment, the frangible material may be a frangible metal material, such as, for example, aluminium.

In embodiments, the templates 10, 30, 104a-104z may have a thickness that is substantially thin and/or sized, configured or adapted such that the templates 10, 30, 104a-104z may be broken or separated into pieces or fragments, without the use of a tool, by hands of user. In embodiments, the first portion of the templates 10, 30, 104a-104z may have the substantially thin thickness and the second portion may have a substantially thicker thickness than the thickness of the first portion such that the first portion of the templates 10, 30, 104a-104z may be fragmented, broken or separated away from the second portion, without the use of a tool, by hands of the user. The thickness of the templates 10, 30, 104a-104z or the first portions of the templates 10, 30, 104a-104z may be in the range of about 0.5 mm to about 4.0 mm. In embodiments, the thickness of the templates 10, 30, 104a-104z may be, for example, less than about 4.0 mm, less than about 3.0 mm, less than about 2.0 mm, less than about 1.5 mm or about 1.0 mm.

In embodiments, one of more of the templates 10, 30, 104a-104z, the bone plate 40 and the corresponding plates may be included in the kit container. However, other components necessary for performing and completing the procedure may also be included in the kit container. For example, other components that may be included in the kit container may be at least one selected from surgical instruments, wires, drill bits, locking screws, non-locking screws, plate bending or contouring systems and reamers. The wires may include, for example, K-wires and/or olive wires, and the reamers may include a distal reamer and/or a reamer for a mediocarpal plate. One or more, or preferably all, of the other components included in the kit container may be housed, protected and/or stored within individual sterile-packaging such that each of the other components of the kit container is sterile, can be easily opened or unpackaged and immediately ready for utilization during the procedure.

Some of the components of the kit container may be single-use components which are disposable after being used during procedure. The type or configuration of one of the templates 10, 30, 104a-104z, the plate 40, the corresponding plates and/or other components that are included in the kit container are determined, identified and/or selected based on a type of surgery or operation that is necessary or needed by the patient. For example, different kits containers include different templates 10, 30, 104a-104z, different plates 40, different corresponding plates and/or different other components based on different types of bone-fixation or implantation surgeries that are necessary or needed by different patients.

The individual sterile-packaging that houses, stores and protects the templates 10, 30, 104a-104z, the plate 40, the corresponding plates and other components of the kit container may be packed in clear sterile-packaging so that contents of each individual sterile-packaging may be visible to allow for quick and easy identification of the contents during surgeries or medical procedures. Additionally, the individual sterile-packaging may, in embodiments, display markings or indicia and/or have color coding which may be indicative of the contents of the packaging. As a result, the markings, indicia and/or color coding may simplify handling and provide easy recognition of the contents during the procedure. In embodiments, the individual sterile-packaging may contain, have or display, for example, one or more scanable images to facilitate quick, easy and reliable identification of the contents of the packaging along with facilitating automated tracking, ordering and/or re-ordering of specific components of the kit container when such specific components have been depleted or utilized during the procedure. In an embodiment, each individual sterile-packaging may have one or more bar codes and/or quick response codes that are indicative of the contents of each packaging. The present disclosure should not be deemed limited to a specific embodiment of markings, indicia, color coding and/or one or more scanable images displayable on the individual sterile-packaging.

As shown in FIGS. 1 and 2, each of the templates 10, 30 have a length defined between a first end 12 and a second end 14 (collectively known hereinafter as "first and second ends 12, 14") that is located opposite to the first 12, and a thickness defined between a top side 16 and a bottom side 18 located opposite to the top side 16. The length of each of the templates 10, 30 may be the same as, similar to or correspond to the length of the longest plate that may be included in the kit container of each of the templates 10, 30. For example, the template 30 may have a length that corresponds to the length of the longest plate in the kit container including the template 30, which may be, for example, the plate 40 as shown in FIG. 4.

Each of the templates 10, 30, 104a-104z may have a general shape and/or an outer perimeter 19 (collectively known hereinafter as "perimeter 19") which may extend the entire length of the templates 10, 30, 104a-104z and may include both the first and second ends of each of the templates 10, 30, 104a-104z. The perimeter 19 of each of the systems 10, 30, 104a-104z may be shaped, adapted or configured to correspond to, be the same as, or substantially the same as a general shapes and/or outer perimeters of the plurality of bone plates that are included in the kit container along with the templates 10, 30, 104a-104z. For example, the perimeter 19 of the systems 10, 30, 104a-104z may correspond to the general shapes and/or outer perimeters of a first plurality of bone plates (not shown in the drawings) that are included in a first kit container along with the template 10, and the perimeter 19 of the template 30 may correspond to the general shapes and/or outer perimeters of a second plurality of bone plates (not shown in the drawings) that are included in a second kit container along with the template 30 and the plate 40. Further, the general shapes and/or outer perimeters of the first plurality of bone plates of a first kit container may or may not be the same as or similar to the general shapes and/or outer perimeters of the second plurality of bone plates of a second kit container. Moreover, the first plurality of bone plates may or may not different bone plate implants than bone plate implants of the second plurality of bone plates.

In embodiments, the template 10 may have a base section 20 is located adjacent to the first end 12 and a removable segment section 22 that is located adjacent to the second end 14 as shown in FIG. 1. Further, the perimeter 19 of the template 10 may comprise the outer perimeters of the base section 20 and/or the removable segment section 22. In embodiments, the template 30 may be free of a base section and may have a removable segment section (not shown in the drawings) which extends the entire length of the template 30 between the first and second ends 12, 14 of the template 30 shown in FIG. 2.

The templates 10, 30 and/or the base section 20 and/or the removable segment section 22 of the template 10 may have a cross-sectional shape that may be the same as, similar to and/or corresponds to a cross-sectional shape of at least a portion of a damaged bone of a patient requiring a surgical procedure. Further, the cross-sectional shape of the templates 10, 30, at least a portion of the templates 10, 30, and/or the base sections 20 and the removable segment section 22 of the template 10 may be a shape similar to a circle, an oval, a square, a rectangle, a triangle, a polygon, and/or combinations thereof. Moreover, the cross-sectional shape may have or be made of one or more lines selected from the group consisting of straight lines, curved lines, angled lines, parallel lines, perpendicular lines and combinations thereof.

In embodiments, the base section 20 and/or the removable segment section 22 of the template 10 may be made of the at least one frangible material such that the template 10, the base section 20 of the template 10 and/or the removable segment section 22 of the template 10 may be broken or separated into pieces or fragments, without the use of a tool, by hands of user. In other embodiments, the base section 20 and/or the removable segment section 22 of the template 10 may have the substantially thin thickness that is sized, configured and adapted such that the template 10, the base section 20 of the template 10 and/or the removable segment section 22 of the template 10 may be broken or separated into pieces or fragments, without the use of a tool, by hands of user. A portion of the length, or the entire length, of the template 30 may be made of the at least one frangible material and/or may have the substantially thin thickness such that the portion of the length, or the entire length, of the template 30 may be broken or separated into pieces or fragments, without the use of a tool, by hands of user.

The removable segment section 22 of template 10 may have removable segments 24a-24z which may extend from the base section 20 of the template 10 to the second end 14 of the template 10, whereby removable segment 24a is adjacent to the base section 20 and removable segment 24z is adjacent to the second end 14 of the template 10. For example, the template 10 may have a total of seven (7) removable segments 24a-24z that extend from the base section 20 to the second end 14 as shown in FIG. 1. The total number of removable segments 24a-24z which may be included in the removable segment section 22 of the template 10 may depend or be based on the overall length of the longest bone plate (not shown in the drawings) that is included in the kit container along with the template 10. As a result, the length of the template 10, from the first end 12 to the second end 14 may be the same as, similar to or substantially similar to the overall length of the longest bone plate include the kit container along with the template 10.

The template 10 has connection sections 26a-26z that connect, attach and/or affix the removable segments 24a-24z to each other and to the base section 20 of the template 10. The total number of connections sections 26a-26z may correspond to the total number removable segments 24a-24z, the connection section 26a may be located adjacent to the base section 20 and/or the removable segment 24a, and the connection section 26z may be located adjacent to the removable segments 24z and the second end 14 of the template 10. In embodiments, at least the removable segments 24a-24z and/or the connection sections 26a-26z of the template 10 may be made of the at least one frangible material and/or may have the substantially thin thickness such that at least the removable segments 24a-24z and/or the connection sections 26a-26z of the template 10 may be broken or separated into pieces or fragments, without use of a tool or by hands of user.

The connection sections 26a-26z have widths that are less than or smaller than widths of the base section 20 and the removable segments 24a-24z. In embodiments, the widths of the connection sections 26a-26z are sized, configured or adapted such that the connection sections 26a-26z may be broken or separated into pieces or fragments, without use of a tool or by hands of a user. In embodiments, the widths of the connection sections 26a-26z may be greater than about 1 mm, less than about 1 mm or about 1 mm.

As shown in FIG. 2, the removable segments 24a-24z of the template 30 may extend the entire length of the template 30 between the first and second ends 12 and 14 of the template 30. The removable segment 24a may be located adjacent to the first end 12 of the template 30, and the removable segment 24z may be located adjacent to the second end of the template 30. The connection sections 26a-26z may connect, attach and/or affix the removable segments 24a-24z of the template 30 to each other. The connection section 26a may be located adjacent to the first end 12 and may connect the removable segment 24a to the other removable segments of the template 30, and the connection section 26z may be located adjacent to the second end 14 and may connect the removable segment 24z to the other removable segments of the template 30. Similar to the system 10, the widths of the connection sections 26a-26z of template 30 may be sized, configured or adapted such that the connection sections 26a-26z may be broken or separated into pieces or fragments, without use of a tool or by hands of a user.

The plate 40, as shown in FIG. 4, has a length defined between a first end 42 and a second end 44 (collectively known hereinafter as "first and second ends 42, 44") located opposite to the first end 42 of the plate 40. The plate 40 may have a general shape or an outer perimeter 45 (hereinafter "perimeter 45") which may extend the entire length of the plate 40 and may include the first and/or second ends 42, 44 of the plate 40. Moreover, the plate 40 may have screw holes 46 which may extend through the plate 40 and/or along at least a portion of the length, or the entire length, of the plate 40.

In embodiments, the system 10 and the template 30 may have one or more structure features that may correspond to one or more structure features of the suitable plate and the corresponding plates that may be provided in the kit containers with the template 10 or the template 30, respectively. For example, the kit container may include the template 30 and the bone plate 40, and the template 30 may have one or more holes 28 extending through the template 30 which may correspond to the screw holes 46 of the plate 40 as shown in FIGS. 2 and 4.

In an embodiment, the plate 40 may be the longest plate provided in the kit container along with template 30 and the other corresponding plates for completing a bone plate fixation procedure. The corresponding plates may have the same outer perimeter as perimeter 44 of the plate 40, and the perimeter 19 of the template 30 may the same as, similar to or substantially similar to the perimeter 44 of the plate 40 and/or the perimeter of the corresponding plates. The corresponding plates of the kit container may have different lengths with respect to each other and shorter or smaller lengths with respect to the longest plate, the plate 40.

The number of removable segments 24a-24z of the template 30 depends or is based on the overall length the longest bone plate implant, such as, for example, the plate 40, provided in the kit container for the template 30. As shown in FIGS. 2 and 4, the template 30, in an embodiment, has a total of ten (10) removable segments 24a-24z extending along the length of the template 30 between the first and second ends 12, 14 of the system. The total number of removable segments 24a-24z corresponds to the ten (10) sections each having a screw hole 46 extending along the length of the plate 40 between the first and second ends 42, 44 of the plate 40. The present disclosure should not be deemed as limited to a specific embodiment of the total number of removable segments 24a-24z of the templates 10, 30 or the total number of segments or screw holes of the plate 40 or the corresponding plates.

One method for using the template 10 to determine, identify and select the suitable plate for affixing to a damaged bone of a patient or for implanting into the patient at the operating site comprising delivering the kit container to the surgeon, surgical staff or medical provider. The delivered kit container may include the template 10, a longest bone plant implant and corresponding bone plate implants, each have lengths that are different from one another and shorter than the length of the longest bone plate implant included in the kit container. Each component of the kit container is wrapped or packaged in individual sterile-packaging and the template 10 has a shape that corresponds to at least a portion of the longest bone plate and corresponding bone implants. Moreover, the template 10 has an overall length that corresponds to the overall length of the longest bone plate implant included in the kit container.

The template 10 is unpackaged from the individual sterile-packaging and the user of the template 10 holds or positions the template 10 next to, near and/or adjacent to the operating site or the damaged bone on the patient. The user visually compares the length of the operating site or the damaged bone to the length of the template 10 to determine or identify the suitable length for the suitable plate that is needed to successfully complete the surgical procedure. If the suitable length, based on the length of the operating site and/or the damaged bone, corresponds to the overall length of the longest bone plate implant of the kit container, then the longest bone plate implant of the kit container is determined and/or identified to be the suitable plate used to complete the surgical procedure. Then, the longest bone plate implant is unpackaged from its individual sterile-packaging and utilized by the surgeon to complete the surgical procedure, and the template 10 is disposed of after the suitable plate is determined.

However, if the suitable length, based on the visual inspection or comparison of the length of the operating site and/or the damaged bone, is shorter than overall length of the longest bone plate implant provide in the kit container, then the user may utilize the system 10 to determine the suitable length which is then utilized to identify and select the suitable plate from the corresponding plates provided in the kit container. The user may determine, via visual comparison and/or inspection, that the length of the operating site and/or the damaged bone is the same as, equal to or similar to a portion of length of the template 10. It may be determined by the user that the length of the operating site and/or the damaged bone may correspond to a remaining length of the template 10 after one or more removable segments 24a-24z may be removed from the template 10 or removed from the base section 20 and the removable section 22 of the template 10. The user may, by hand and without use of a tool, brake, remove or separate the one or more removable segments 24a-24z from the template 10 at one of the connecting sections 26a-26z such that the template 10 has a remaining length that corresponds to the length of the operating site and/or the damaged bone of the patient. As a result, the remaining length of the template 10 corresponds to the suitable length for the suitable plate to successfully complete the surgical procedure.

Figure 3:
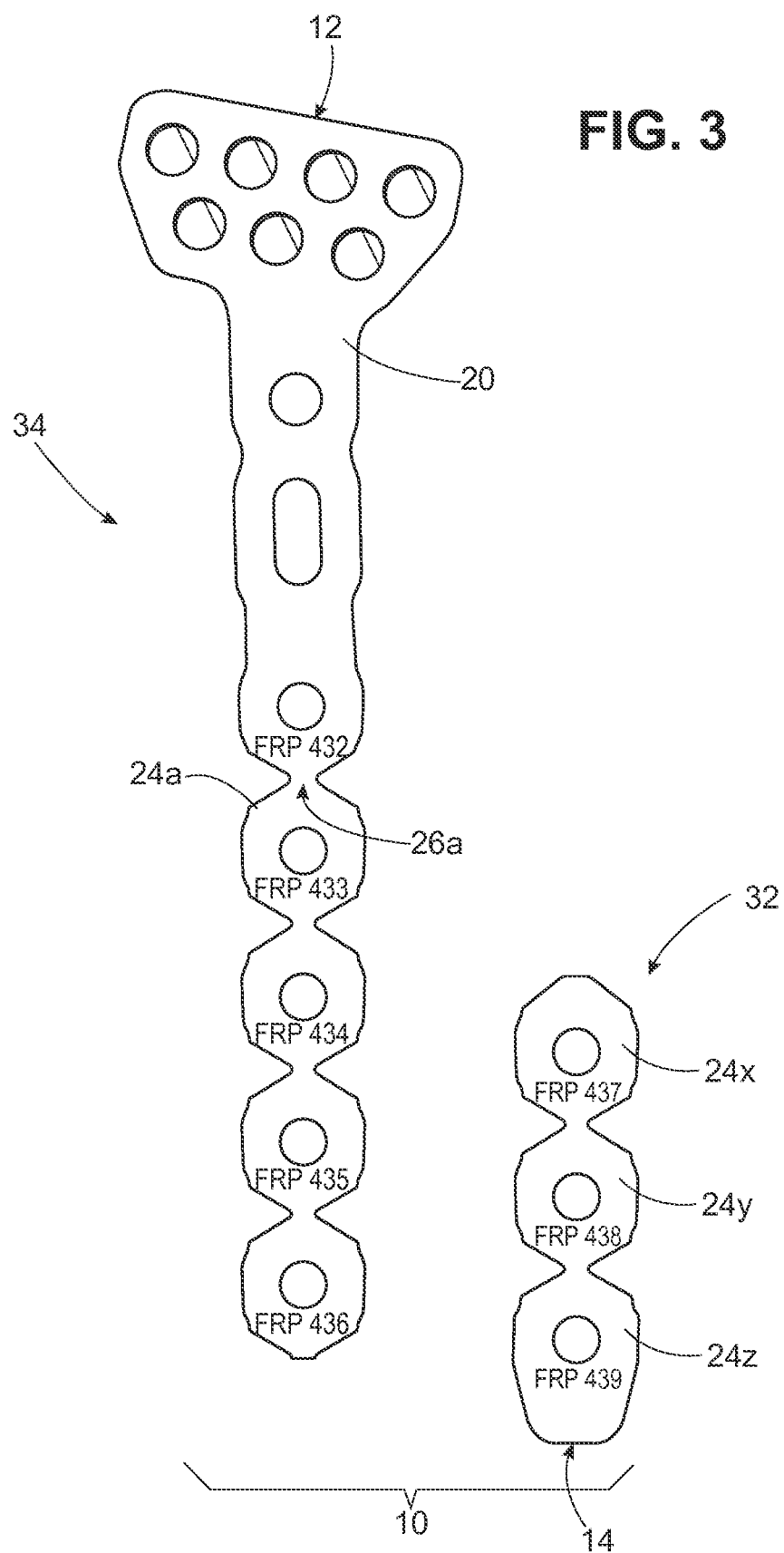
FIG. 3 illustrates a top plan view of a bone plate template system having removable segments separated from a bone plate template system in an embodiment.

Each of the body section 20 and the removable segments 24a-24z of template 10 and each of the removable segments 24a-24z of template 30 display indicia that is indicative of the longest and corresponding bone plate implants provided in the kit container. For example, the indicia displayed on the body section 20 of the template 10 is indicative of the shortest bone plate implant provided in the kit container, and the indicia displayed on the removable segment 24z is indicative of the longest bone plate implant provided in the kit container. The indicia displayed on each of the removable segments 24a-24y located between the body section 20 and the removable segment 24z is indicative of a corresponding bone plate implant of the kit container having a length greater than the shortest bone plate implant and less than the longest bone plate implant, respectively, as shown in FIGS. 1 and 3.

Indicia displayed on the templates 10, 30 may be, for example, letters, numbers, symbols, designs, graphics and/or combinations thereof. The indicia may be marked onto a top side and/or a bottom side of the templates 10, 30 by a known marking technique. For example, the indicia may be stamped, printed, engraved, cut or carved into one or more of the top and bottom sides of the templates 10, 30. In a preferred embodiment, the indicia is laser-marked into the top surface of the templates 10, 30 by known laser-marking techniques. It should be understood that the present disclosure is not limited to a specific embodiment of the indicia and/or the known marking technique used to mark the indicia onto the templates 10, 30.

Because the remaining length of the template 10 corresponds to the length of the operating site and/or the damaged bone of the patient, the removable segment 24x that was separated from the template 10 and that is located opposite to the second end 14 of the template 10 also corresponds to the length of the operating site and/or damaged bone. Moreover, the indicia displayed on the removable segment 24x is indicative of the suitable plate having the suitable length that is the same as, similar to or corresponding to the length of the operating site and/or the damaged bone of the patient.

A user, surgical staff member or medical provide may visually inspect the indicia displayed on the removable segment 24x, located opposite to the second end 14 of the template 10, which is indicative of the suitable plate for completing the surgical procedure and is indicative of the corresponding bone plate implant of the kit container that has a length that corresponds to the suitable length and the length of the operating site and/or the damaged bone of the patient. After the corresponding bone plate implant that is determined to be the suitable plate is identified from the corresponding plates provided in the kit container, the suitable plate is selected and removed from the kit container to be used to complete the surgical procedure. The suitable plate may then be unpackaged from the individual sterile-packaging and utilized by the surgeon to complete the surgical procedure, and the template 10 along with the separated removable sections 24x-24z may be disposed of without any further attention from the surgical staff or medical provider.

For example, as shown in FIG. 1, the indicia displayed on the base plate 20 of the template 10 may include letters and numbers, such as, for example, "FRP 432", and the indicia displayed on removable segments 24a-24z may include letters and increasing numbers, such as, for example, "FRP 433" to "FRP 439", respectively. The user physically, without use of a tool, removes or separates the removable segments 24x-24z (collectively known hereinafter as "separated portion 32") from the template 10 so that the remaining length of a remaining portion 34 of the template 10 has a length that is the same as, similar to or corresponding to the length of the operating site and/or the damaged bone and the suitable length for the suitable plate to complete the surgical procedure as shown in FIG. 3. The user, a surgical staff member or medical reads the indicia displayed on the removable segment 24x that is located opposite to the second end 12 of the separated portion 32. In this example, the indicia "FRP 437" displayed on the removable segment 24x is read and used to determine and identify which bone plate implant provided in the kit container is the suitable plate having the suitable length for completing the surgical procedure. Each individual sterile-packaging, containing one bone plate implant, displays indicia that correspond to or match the indicia displayed on one of the base portion 20 or one of the removable segments 24a-24z of the template 10. After the individual sterile-packaging that displays the indicia "FRP 437" is identified and removed from the kit container, the suitable bone plate implant is removed from its sterile-packaging and utilized by the surgeon to complete the surgical procedure, and the separated portion 32 and the remaining portion 34 are readily disposed of without further attention by the surgical staff or medical provider.

Similar to the indicia displayed on the template 10 and as shown in FIG. 2, the indicia displayed on each of the removable segments 24a-24z of the template 30 may be indicative of one bone plate implant having a different length that is provided in a kit container for the template 30. The indicia displayed on the template 30 may include, for example, sets of letters, such as "FPR" and sets of different numbers, such as, "704," "705," "706," "707," "708," "709," 710, "712," "714," and "716". Each set of letters and numbers displayed on the template 30 may be indicative of one bone plate implant that is provided in the kit container for the template 30. It should be understood that the present disclosure is not limited to a specific embodiment of the indicia displayed on the templates 10, 30 and/or on the individual sterile-packaging protecting each bone plate implant provided in the kit container. Moreover, the indicia displayed on the templates 10, 30 and/or on the individual sterile-packaging provided in the kit may be any indicia as known to one of ordinary skill in the art.

In embodiments, a method of using the template 30 to determine and identify the suitable plate for a bone plate fixation procedure may comprise the user placing the template 30 adjacent to the operating site of the patient. After visually comparing the length of the template 30 to the operating site, the user may rip, tear or separate removable segments 24e-24z away from the template 30, based on the suitable length for the suitable plate identified by the visual inspection and/or comparison of the operating site or damaged bone of the patient. The user, a surgical staff member or medical provider may read the indicia "FPR 706" displayed on the separated removable segment 24e and subsequently locate and remove the individual sterile-packaging displaying the indicia "FPR 706" from the kit container. The surgeon may removed the suitable plate, having the suitable length, from the removed sterile-packaging and use the suitable plate for completing the bone plate fixation procedure, and the removed sterile-packaging and separated portions of the system 30 may be proper disposed of by the surgical staff member or medical provider.

FIG. 5 shows the system 100 having a main body 101 with the templates 104a-104z arranged, positioned, and/or located around a perimeter 102 of the main body 101. Each of the templates 104a-104z may be removably attached, connected and/or affixed to the perimeter 102 of the main body 101. As a result, each of the templates 104a-104z may be removable attached, connected and/or affixed to each other via the main body 101. In embodiments, one or more of the templates 104a-104z may be removably attached, connected and/or affixed to at least one of the other templates 104a-104z. In embodiments, the system 100 may have one or more removable segments 24a-24z which may connect one or more templates 104a-104z to at least one of the other templates 104a-104z and/or to the main body 101. For example, a template 104b may be removable attached, connected and/or affixed to a template 104c by removable segment 24a as shown in FIG. 5. Similar to templates 10, 30, one or more of the templates 104a-104z may have one or more of the removable segments 24a-24z.

The system 100 may have connection points 106 which may be removably connect, attach and/or affix one or more of the templates 104a-104z to the perimeter 102 of the main body 101. In embodiments, at least two connection points 106 may removably connect, attach and/or affix each of the templates 104a-104z to the main body 101 of the system 100 as shown FIG. 5. Each of the connections points 106 of the system 100 may include at least one protrusion formed on the main body 101 of the system 100 and at least one recession formed on each of the templates 104a-104z. In embodiments, the system 100, the main body 101, one or more of the templates 104a-104z, the connection points 106, the at least one protrusion of each connection point 106 and/or the recession of each connection point 106 may be made of the at least one frangible material such that one or more of the main body 101, the templates 104a-104z and/or the connection points 106 may be broken or separated into pieces or fragments, without the use of a tool, by hands of user. In an embodiment, portions of the system 100 may be made of the at least one frangible material such that portions of the system 100 may be broken or separated into pieces or fragments, without the use of a tool, by hands of user.

The system 100 may be housed, stored or protected in the individual sterile-packaging and may be provided in the kit container for completing the procedure. Each of the templates 104a-104z may have a different shape and/or size when compared to the shapes and sizes of the other templates 104a-104z of the system 100. Each of the templates 104a-104z may have a shape and size that may correspond to a corresponding bone plate implant (not shown in the drawings) provided in the kit container. Each of the templates 104a-104z may have a general shape, outer perimeter, width and/or length that may be the same as, similar to or corresponding to a general shape, outer perimeter, width and/or length of at least one corresponding bone plate implant provided in the kit container. For examples, templates 104a, 104b, 104c, 104d, 104e, 104f, 104x, 104y, 104z may have different shapes and/or that correspond to the different shapes and/or sized of nine different bone plate implants provided in the kit container. In an embodiment, the system 100 may include a total number of fourteen (14) differently shaped and sized bone plate templates as shown in FIG. 5. The total number of bone plate templates 104a-104z of the system 100 may be any total number of bone plate templates as known to one of ordinary skill in the art.

Similar to templates 10, 30, the templates 104a-104z may have one or more of the removable segments 24a-24z which may be removed and/or separated therefrom based on size, shape and/or length of the operating site or damaged bone of the patient. The user may unpackage the system 100 from the individual sterile-packaging and position the system 100 near or adjacent to the operating site of the patient to make a visual comparison or determination of the templates 10, 30 with respect to the size, shape and/or length of the operating site or damaged bone of the patient. Based on the visual comparison or determination, the user may select one of the templates 104a-104z, having a suitable size, shape and/or length with respect to the operating site or damaged bone, to be the suitable bone plate template (hereinafter "suitable template") from the system 100. The user may remove or separate the suitable bone plate template from the system 100 via the connecting points 106, without use of a tool, by hands of the user.

The user may position the suitable template adjacent to or near the operating site or damaged bone to make a visual comparison or determination of the length and/or width of the suitable template with respect to the length and width of the operating site or damaged bone. Based on the visual comparison or determination, the user may determine that one or more of the removable segments 24a-24z of the suitable bone plate template must be removed or separated such that the remaining portion of the suitable template has a suitable length and/or width when compared to the length and/or width of the operating site or damaged bone.

Similar to templates 10, 30 and removable segments 24a-24z of the templates 10, 30, the templates 104a-104z and/or the removable segments of the system 100 may stamped or marked with or may display the indicia. The indicia of each of the templates 104a-104z and/or the removable segments of the system 100 may be indicative of one bone plate implant, provided in the kit container, which has a corresponding shape, size and/or length with respect to shape, size and/or length of each template 104a-104z. In other words, each of the different sized and/or shaped templates 104a-104z correspond to differently sized and/or shaped bone plate implants provided in the kit container, and the indicia displayed on each of the differently sized and/or shaped templates 104a-104z is indicative the corresponding differently sized and/or shaped bone plate implants.

After the suitable template is selected from the templates 104a-104z of the system 100 by the user. The indicia displayed on the suitable template may be utilized, observed and/or inspected to determine and/or identify the corresponding suitable bone plate implant from the plurality of bone plate implants provided in the kit container. After the suitable bone plate implant is identified, the suitable bone plate implant may be removed from the kit container, unpackaged from its individual sterile-packaging and utilized to complete the bone plate fixation or implantation procedure. The unused portion(s) of the system 100, excluding the suitable template, may be discarded without further attention from the surgical staff or medical provider.

For example, the user may determine that the suitable template comprises templates 104b, 104c and removable segment 24a as shown in FIG. 5. The user may remove the suitable template from the system 100 and may position the suitable template adjacent to the operating site of the patient. Based on visual comparison of the length of the suitable template and the length of the operating site, the user may remove or separate the removable segment 24a and the template 104c from the template 104b because the template 104b may have the suitable length when compared to the length of the operating site of the patient. The separated or removed removable segment 24a and the template 104c may be discarded and the remaining portion of the suitable template, i.e., template 104b, may be utilized to determine, identify and/or select the suitable plate from the plurality of bone plate implants provided in the kit container. For example, the indicia on suitable template 104b may include "FHF 408" which may be indicative of a corresponding suitable bone plate implant provided in the kit container. After the suitable bone plate implant is identified by the indicia displayed on the suitable template 104b, the suitable bone plate implant may be removed from the kit container, unpackaged from its individual sterile-packaging and utilized to complete the procedure.

It will be appreciated that several of the above-disclosed and other features and functions, or alternatives thereof, may be desirably combined into many other different systems and/or methods. Also, various presently unforeseen or unanticipated alternatives, modifications, variations or improvements therein may be subsequently made by those skilled in the art, and are also intended to be encompassed by the present disclosure.

I claim:

1. A bone plate template for identifying a suitable bone plate implant, the bone plate template comprising:
   a length defined between a first end of the bone plate template and a second end of the bone plate template located opposite to the first end of the bone plate template, wherein at least a portion of the length of the bone plate template has a shape that corresponds to at least a portion of a shape of the suitable bone plate implant;
   a first portion of the bone plate template having a first width and located adjacent to the first end of the bone plate template;
   at least one first removable segment of the bone plate template having a second width and located adjacent to the second end of the bone plate template; and
   at least one connecting section of the bone plate template connecting the first portion to the at least one first removable segment, wherein the at least one connecting section has a third width that is less than the first width of the first portion and the second width of the at least one removable segment;
   wherein the bone plate template has a thickness and is made of a frangible material, and wherein the thickness of the bone plate template, the frangible material of the bone plate template or the third thickness of the at least one connecting section is configured such that the bone plate template is breakable at the at least one connecting section without use of a tool.

2. The bone plate template according to claim 1, further comprising:
   first indicia displayed on the at least one first removable segment, wherein the first indicia is indicative of a first bone plate implant having a first length.

3. The bone plate template according to claim 2, further comprising:
   at least one second removable segment located between and connected to the first portion and the at least one first removable segment.

4. The bone plate template according to claim 3, further comprising:
   second indicia displayed on the at least one second removable segment, wherein the second indicia is indicative of a second bone plate implant having a second length that is less than the first length of the first bone plate implant.

5. The bone plate template according to claim 4, wherein third indicia is displayed on the bone plate template that is indicative of a third bone plate implant having third length that is less than the first length of the first bone plate implant and the second length of the second bone plate implant.

6. The bone plate template according to claim 1, wherein the bone plate template is stored within individual sterile-packaging.

7. A bone plate template system for determining a suitable bone plate implant from a plurality of bone plate implants, the system comprising:
   a first bone plate implant having a first length;
   a second bone plate implant having a second length that is less than the first length of the first bone plate implant;
   a bone plate template having a shape and a length defined between a first end and a second end located opposite to the first end, wherein at least a portion of the shape of the bone plate template corresponds to at least portions of a shape of at least one of the first and second bone plate implants, wherein the bone plate template comprises at least one removable segment located adjacent to the second end of the bone plate template, wherein a connecting section of the bone plate template has a width and connects the at least one removable segment to the first end of the bone plate template, wherein the bone plate template displays first indicia indicative of the first bone plate and the at least one removable segment displays second indicia indicative of the second bone plate;
   wherein the bone plate template is made of a frangible material such that the at least one removable segment is separable from the bone plate template without use of a tool.

8. The system according to claim 7, wherein the width of the connecting section is less than other widths of the bone plate template located between first and second ends of the bone plate template.

9. The system according to claim 7, wherein the first length of the first bone plate implant is less than the second length of the second bone plate implant.

10. The system according to claim 7, wherein each of the first bone plate implant, the second bone plate implant and the bone plate template are individually packaged in sterile-packaging.

11. A bone plate template system for determining a suitable bone plate implant from a plurality of bone plate implants, the system comprising:
   a first removable bone plate template, wherein at least a portion of a shape of the first removable bone plate template corresponds to at least a portion of a shape of a first bone plate implant; and
   a second removable bone plate template removably connected to the first removable bone plate template, wherein at least a portion of a shape of the second removable bone plate template corresponds to at least a portion of the a shape of a second bone plate implant, wherein the shape of the first removable bone plate template is different than the shape of the second removable bone plate template.

12. The system according to claim 11, wherein the first removable bone plate template or the second removable bone plate template comprises one or more removable segments.

13. The system according to claim 11, further comprising:
   a main body removably connecting the first and second removable bone plate templates.

14. The system according to claim 13, wherein the main body has connecting points removably connecting the first and second removable bone plate templates to the main body.

15. The system according to claim 11, further comprising:
   at least one removable segment removably connecting the first and second removable bone plate templates.

16. The system according to claim 11, further comprising:
   first indicia, displayed on the first removable bone plate template, indicative of the first bone plate implant; and
   second indicia, displayed on the second removable bone plate template, indicative of the second bone plate implant.

* * * * *